(12) United States Patent
Lin et al.

(10) Patent No.: US 10,898,429 B2
(45) Date of Patent: Jan. 26, 2021

(54) USES OF COFFEE PULP EXTRACT

(71) Applicant: TCI CO., LTD, Taipei (TW)

(72) Inventors: Yung-Hsiang Lin, Taipei (TW); Zih-Yi Li, Taipei (TW)

(73) Assignee: TCI CO., LTD, Taipei (TW)

( * ) Notice: Subject to any disclaimer, the term of this patent is extended or adjusted under 35 U.S.C. 154(b) by 145 days.

(21) Appl. No.: 16/241,722

(22) Filed: Jan. 7, 2019

(65) Prior Publication Data

US 2019/0216719 A1    Jul. 18, 2019

Related U.S. Application Data

(60) Provisional application No. 62/617,491, filed on Jan. 15, 2018.

(30) Foreign Application Priority Data

Dec. 27, 2018    (TW) .............................. 107147475 A

(51) Int. Cl.
| | | |
|---|---|---|
| *A61K 36/74* | (2006.01) | |
| *A61K 8/9789* | (2017.01) | |
| *A61Q 19/02* | (2006.01) | |
| *A61Q 19/08* | (2006.01) | |
| *A61K 9/00* | (2006.01) | |
| *A61P 17/00* | (2006.01) | |

(52) U.S. Cl.
CPC .......... *A61K 8/9789* (2017.08); *A61K 9/0014* (2013.01); *A61K 9/0019* (2013.01); *A61K 9/0053* (2013.01); *A61K 9/0095* (2013.01); *A61K 36/74* (2013.01); *A61P 17/00* (2018.01); *A61Q 19/02* (2013.01); *A61Q 19/08* (2013.01); *A61K 2236/331* (2013.01)

(58) Field of Classification Search
CPC ....................................................... A61K 36/74
See application file for complete search history.

(56) References Cited

FOREIGN PATENT DOCUMENTS

| | | | |
|---|---|---|---|
| CN | 1980635 B | 4/2015 | |
| FR | 2991583 A1 * | 12/2013 | ............. A61Q 19/08 |
| WO | WO 2017/040810 A1 | 3/2017 | |
| ZA | 200608698 B | 7/2008 | |

OTHER PUBLICATIONS

Kumar, Vinod, et al., "A keratin scaffold regulates epidermal barrier formation, mitochondrial lipid composition, and activity," *J. Cell Biol.*, vol. 211, No. 5, pp. 1057-1075 (2015).

Pereda, Maria Del Carmen Velazquez, et al., "Expression of differential genes involved in the maintenance of water balance in human skin by *Piptadenia colubrin* extract," *Journal of Cosmetic Dermatology*, vol. 9, Issue 1, pp. 35-43 (2010).

(Continued)

*Primary Examiner* — Rosanne Kosson
(74) *Attorney, Agent, or Firm* — Christensen, Fonder, Dardi & Herbert PLLC

(57) ABSTRACT

A method for at least one of whitening skin, improving skin condition, protecting skin and inhibiting skin aging is provided, wherein the method comprises administering to a subject in need an effective amount of a coffee pulp extract. A method for at least one of repairing skin tissues, preventing skin disease, and treating skin disease is also provided, wherein the method comprises administering to a subject in need an effective amount of a coffee pulp extract.

4 Claims, 7 Drawing Sheets
(1 of 7 Drawing Sheet(s) Filed in Color)

(56) References Cited

OTHER PUBLICATIONS

Sandilands, Aileen, et al., "Filaggrin in the frontline: role in skin Barrier function and disease," *Journal of Cell Science*, vol. 122, Issue 9, pp. 1285-1294 (2009).
Sayo, Tetsuya, et al., "Hyaluronan Synthase 3 Regulates Hyaluronan Synthesis in Cultured Human Keratinocytes," *The Journal of Investigative Dermatology*, vol. 118, pp. 43-48 (2002).
Kabashima, Kenji, "New concept of the pathogenesis of atopic dermatitis: Interplay among the barrier, allergy, and pruritus as a trinity," *Journal of Dermatological Science*, vol. 70, pp. 3-11 (2013).
McGrath, John A., et al., "The filaggrin story: novel insights into skin-barrier function and disease," *TRENDS in Molecular Medicine*, vol. 14, No. 1, pp. 20-27.
Borkowski, Andrew W., "Toll-like receptor 3 activation is required for normal skin barrier repair following UV damage," *Journal of Investigative Dermatology*, vol. 135, Issue 2, pp. 569-578 (2015).
Murthy, Pushpa S., et al., "Recovery of Phenolic Antioxidants and Functional Compounds from Coffee Industry By-Products," *Food Bioprocess Technol*, vol. 5, pp. 897-903 (2012).
Duangjai, Acharaporn, et al., "Comparison of antioxidant, antimicrobial activities and chemical profiles of three coffee (*Coffee arabica* L.) pulp aqueous extracts," *Integrative Medicine Research*, vol. 5, pp. 324-331 (2016).
Someya, Takao, et al., "Fibroblast and keratinocyte gene expression following exposure to extracts of neem plant (*Azadirachta indica*)," *Data in Brief*, vol. 16, pp. 982-992 (2018).
Rodrigues, Francisca, et al., "In vitro and in vivo comparative study of cosmetic ingredients Coffee silverskin and hyaluronic acid," *Experimental Dermatology*, vol. 25, pp. 572-574 (2016).

\* cited by examiner

USES OF COFFEE PULP EXTRACT

CROSS REFERENCE TO RELATED APPLICATIONS

This application claims priority to U.S. Provisional Application Ser. No. 62/617,491 filed on Jan. 15, 2018, in the United States Patent and Trademark Office, and to Taiwan Patent Application No. 107147475 filed on Dec. 27, 2018, in the Taiwan Intellectual Property Office, the disclosures of which are incorporated herein in their entirety by reference.

FIELD OF THE INVENTION

The present invention relates to the use of a coffee pulp extract, especially using coffee pulp extract in whitening skin, improving skin condition, protecting skin, anti-skin aging, repairing skin tissues, preventing skin disease and/or treating skin disease.

BACKGROUND OF THE INVENTION

Glycosylation is a chemical reaction in which glucose is attached to a protein and advanced glycation end products (AGEs) are thus generated. The AGEs accumulated in skin cells may not only lead to the denaturation of proteins that results in the skin aging phenomena (e.g., generation of skin wrinkles and skin aging), but also lead to the production of reactive oxygen species (ROS) and oxidative stress those result in DNA damage and affect DNA's function in skin cells and even induce skin diseases.

Coffee originates from Africa and belongs to the order Rubiaceae and the family Gentianales. In each coffee fruit, there are two coffee beans, which are wrapped in a parchment (also known as a husk, endocarp or pod). The name "parchment" was given because the appearance of dried parchment looks like a sheepskin paper. The structure outside the parchment includes, from inside to outside: mucilage (also known as mucous membrane or honey), pulp and outer skin. In the process of coffee production, only the coffee beans are taken and subjected to a roasting treatment, and the remaining (e.g., pulps) is usually discarded as useless waste.

Inventors of the present invention surprisingly discovered that the coffee pulp extract is effective in inhibiting oxidative stress and increasing the expressions of skin moisturizing genes. Inventors of the present invention also discovered through human clinical trials that coffee pulp extract is effective in reducing melanin in skin, reducing spots on skin, enhancing skin brightness, increasing water content of skin, and increasing skin elasticity quickly. According to the foregoing discovery, coffee pulp, which was regarded as waste, can be used for whitening skin, improving skin condition, protecting skin, inhibiting skin aging, repairing skin tissues, preventing skin disease and treating skin disease.

SUMMARY OF THE INVENTION

An objective of the present invention is to provide a use of a coffee pulp extract in at least one of whitening skin, improving skin condition, protecting skin, and inhibiting skin aging. Preferably, the extract is provided by extracting coffee pulp with a polar solvent, and the polar solvent is selected from a group consisting of water, C1-C4 alcohols, and combinations thereof. Preferably, the extract is used for at least one of moisturizing skin, tightening skin, reducing skin fine lines, alleviating dry skin, enhancing skin brightness, and assisting in maintenance of skin health. Preferably, the extract is taken through a transdermal or oral route.

Another objective of the present invention is to provide a use of the aforesaid coffee pulp extract in the manufacture of a pharmaceutical composition, wherein the pharmaceutical composition is for at least one of repairing skin tissues, preventing skin disease, and treating skin disease. Preferably, the pharmaceutical composition is for inhibiting protein glycosylation in skin cells, and/or decreasing oxidative stress-induced damage to skin cells. Preferably, the skin disease is a disease related to dry skin (e.g., ichthyosis). Preferably, the pharmaceutical composition is provided in a form for oral administration, transdermal administration, or subcutaneous injection.

Still another objective of the present invention is to provide a use of the aforesaid coffee pulp extract in the manufacture of a pharmaceutical composition, wherein the pharmaceutical composition is for increasing the expression of at least one of KRT1 gene, KRT14 gene, AQP3 gene, FLG gene, GBA gene HAS2 gene and HAS3 gene. Preferably, the pharmaceutical composition is provided in a form for oral administration, transdermal administration, or subcutaneous injection.

Yet another objective of the present invention is to provide a method for at least one of whitening skin, improving skin condition, protecting skin, and inhibiting skin aging, comprising administering to a subject in need an effective amount of the aforesaid coffee pulp extract. In the method of the present invention, the coffee pulp extract can be administered to the subject as a skin care product, a health food product, or a beauty beverage. Preferably, the method is for moisturizing skin, tightening skin, reducing skin fine lines, alleviating dry skin, enhancing skin brightness, and/or assisting in maintenance of skin health.

Yet another objective of the present invention is to provide a method for at least one of repairing skin tissues, preventing skin disease, and treating skin disease, comprising administering to a subject in need an effective amount of the aforesaid coffee pulp extract. In the method of the present invention, the coffee pulp extract can be administered to the subject as a pharmaceutical composition. Preferably, the method is for inhibiting protein glycosylation in skin cells, and/or decreasing oxidative stress-induced damage to skin cells. For example, the method is for preventing or treating a disease related to dry skin (e.g., ichthyosis).

Yet another objective of the present invention is to provide a method for increasing the expressions of KRT1 gene, KRT14 gene, AQP3 gene, FLG gene, GBA gene HAS2 gene and/or HAS3 gene, comprising administering to a subject in need an effective amount of the aforesaid coffee pulp extract. In the method of the present invention, the coffee pulp extract can be administered to the subject as a pharmaceutical composition.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

The patent application contains at least one drawing executed in color. Copies of this patent with color drawing(s) will be provided by the Patent and Trademark Office upon request and payment of the necessary fee.

FIG. 3A and FIG. 3B show the effect of the coffee pulp extract of the present invention on increasing skin tightness, wherein FIG. 3A shows the appearances of the gels of "Control group", "AGEs group" and "Extract group" after being suspended in a MEM medium for 6 hours, and FIG. 3B shows the contraction ability of the gels of "AGEs group" and "Extract group", and wherein, the mixture used for preparing the gel of "Control group" did not contain glycosylated BSA and the gel thus obtained was treated with a medium free of coffee pulp extract, the mixture used for preparing the gel of "AGEs group" contained glycosylated BSA and the gel thus obtained was treated with a medium free of coffee pulp extract, and the mixture used for preparing the gel of "AGEs group" contained glycosylated BSA, but the gel thus obtained was treated with a medium that contains the coffee pulp extract (* represents the result is significantly different from that of "AGEs group", $p<0.05$);

FIG. 4, FIG. 5, FIG. 6, FIG. 7 and FIG. 8 show the effects of the coffee pulp extract of the present invention on increasing the expressions of KRT1 gene, KRT14 gene, AQP3 gene, FLG gene, GBA gene, HAS2 gene and HAS3 gene, wherein FIG. 4 shows the expression levels of KRT1 gene and KRT14 gene of cells in each group, FIG. 5 shows the expression level of AQP3 gene of cells in each group, FIG. 6 shows the expression level of GBA gene of cells in each group, FIG. 7 shows the expression level of FLG gene of cells in each group, and FIG. 8 shows the expression levels of HAS2 gene and HAS3 gene of cells in each group, and wherein, the cells in "Control group" were cultured in a medium free of coffee pulp extract, and those in "Extract group" were cultured in a medium that contains the coffee pulp extract (* represents the result is significantly different from that of "Control group", $p<0.05$;  represents the result is significantly different from that of "AGEs group", $p<0.01$; * represents the result is significantly different from that of "AGEs group", $p<0.001$);

DESCRIPTION OF THE PREFERRED EMBODIMENTS

Figure 1:
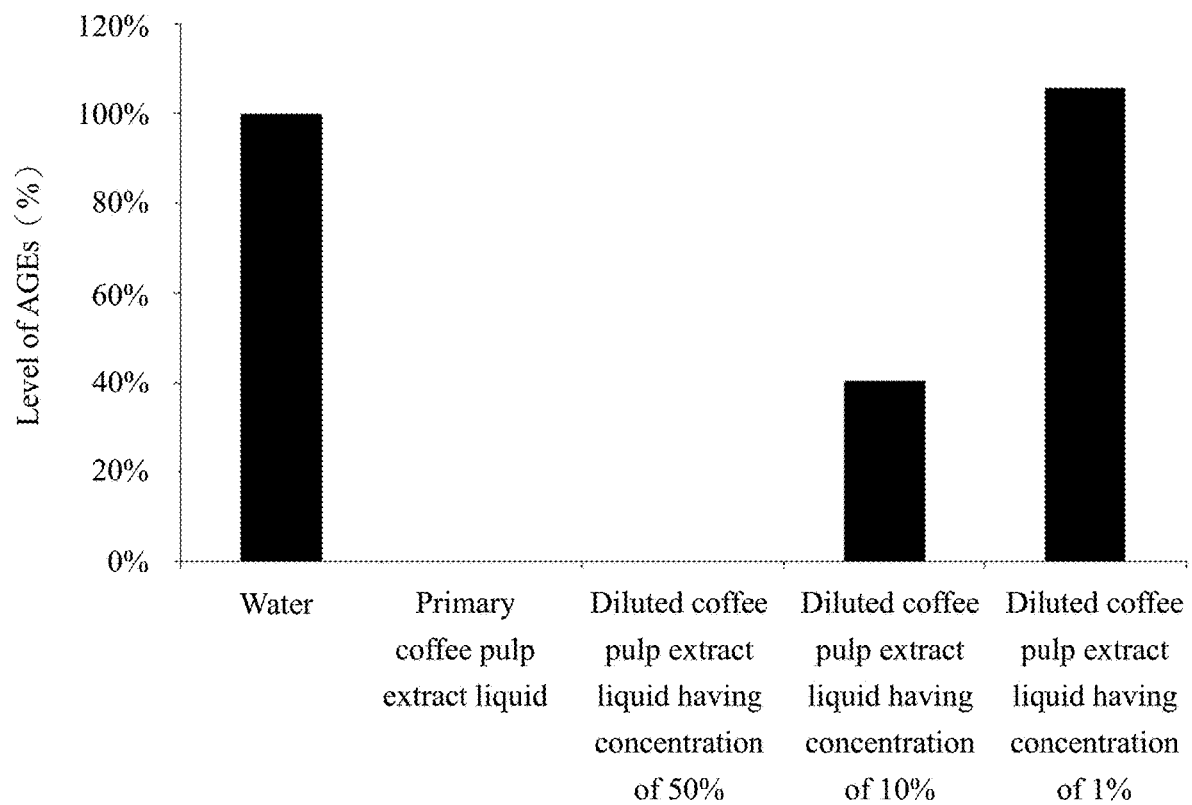
FIG. 1 shows the levels of advanced glycation end products (AGEs) produced by glycosylation of collagen, wherein the glycosylation of collagen was induced in the presence of different concentrations of coffee pulp extract, indicating that coffee pulp extract of the present invention is effective in inhibiting glycosylation (anti-glycosylation)

The following will describe some of the embodiments of the present invention in detail. However, without departing from the spirit of the present invention, the present invention may be embodied in various embodiments and should not be limited to the embodiments described in the specification. In addition, unless otherwise indicated herein, the expressions "a," "an," "the," or the like recited in the specification of the present invention (especially in the claims) are intended to include both the singular and plural forms. The term "treat" or "treating" recited in this specification should not be construed as treating a subject until the subject completely recovered, but should include maintaining the progression or symptoms of the diseases in a substantially static state, increasing the recovery efficiency of a subject, alleviating the severity of a particular condition of illness, or increasing the life quality of patients. The term "prevent" or "preventing" recited in this specification refers to inhibiting or avoiding a particular condition of illness from breaking out, maintaining good health in a sensitive subject, or establishing the ability of a sensitive subject to tolerate diseases. The term "subject" recited in this specification refers to a mammalian, including human and non-human animals.

It was revealed by researches that an increment in the expression levels of KRT1 gene, KRT14 gene, AQP3 gene, FLG gene, GBA gene HAS2 gene and/or HAS3 gene is beneficial to maintenance of cell structure, regulation of water content, enhancement of the production of moisturizing factor NMF, enhancement of hyaluronic acid synthesis, and increase in the water content of cells. It has also been known that the low expression or deletion of aforesaid genes is related to the occurrences of skin aging and/or skin diseases (e.g. a disease related to dry skin such as ichthyosis). These facts can be noted in "A keratin scaffold regulates epidermal barrier formation, mitochondrial lipid composition, and activity. *J. Cell Biol.* 211(5):1057-1075 (2015)," "Hyaluronan Synthase 3 Regulates Hyaluronan Synthesis in Cultured Human Keratinocytes. *The Journal of Investigative Dermatology.* 118: 43-48 (2002)," "Toll-like receptor 3 activation is required for normal skin barrier repair following UV damage. *J Invest Dermatol.* 135(2):569-578 (2015)," "Expression of differential genes involved in the maintenance of water balance in human skin by Piptadenia colubrina extract. *J Cosmet Dermatol.* 9(1):35-43 (2010)," "New concept of the pathogenesis of atopic dermatitis: Interplay among the barrier, allergy, and pruritus as a trinity. *J Dermatol Sci.* 70(1):3-11 (2013)," "The filaggrin story: novel insights into skin-barrier function and disease. *Trends Mol Med.* 14(1):20-27 (2008)," and "Filaggrin in the frontline: role in skin barrier function and disease. *Journal of Cell Science.* 122(9):1285-1294 (2009)," which are entirely incorporated hereinto by reference.

Therefore, if the expressions of KRT1 gene, KRT14 gene, AQP3 gene, FLG gene, GBA gene HAS2 gene and/or HAS3 gene can be increased effectively, the following effects could be provided: assisting in maintenance of skin health, moisturizing skin, tightening skin, reducing skin fine lines, inhibiting skin aging, alleviating dry skin, preventing skin disease, and/or treating skin disease.

Inventors of the present invention discovered that coffee pulp extract is effective in inhibiting glycosylation, inhibiting oxidative stress, and increasing the expressions of skin moisturizing genes (e.g., KRT1 gene, KRT14 gene, AQP3 gene, FLG gene, GBA gene HAS2 gene and HAS3 gene). In addition, inventors of the present invention also discovered through human clinical trials that coffee pulp extract is effective in reducing melanin in skin, reducing spots on skin, enhancing skin brightness, increasing water content of skin, and increasing skin elasticity quickly.

Therefore, the present invention relates to the use of coffee pulp extract, especially relates to using coffee pulp extract in whitening skin, improving skin condition, protecting skin, and/or inhibiting skin aging, using coffee pulp extract in manufacturing a pharmaceutical composition, and providing a method of administering to a subject in need an effective amount of coffee pulp extract. The coffee pulp extract provided in accordance with the present invention is especially for moisturizing skin, tightening skin, reducing skin fine lines, alleviating dry skin, enhancing skin brightness, and assisting in maintenance of skin health. The pharmaceutical composition and method provided in accordance with the present invention are for repairing skin tissues, preventing skin disease, and/or treating skin disease. For example, the skin disease is a disease related to dry skin (e.g., ichthyosis). In addition, the pharmaceutical composition and method provided in accordance with the present invention are also for increasing the expressions of KRT1 gene, KRT14 gene, AQP3 gene, FLG gene, GBA gene, HAS2 gene and/or HAS3 gene.

The coffee pulp extract adopted in accordance with the present invention could be provided by extracting coffee pulp material with a polar solvent, and the polar solvent can be a water, C1-C4 alcohols, or a combination thereof. The amount of the solvent used in the extraction step is not critical and is generally capable of evenly dispersing the materials to be extracted. For example, in the extraction step, the extraction solvent and coffee pulp could be used at a weight ratio ranging from 1:1 to 30:1 (extraction solvent: coffee pulp). In one embodiment of the present invention, 100 g of coffee pulp was placed in a container, and then 2000 mL of water was added thereinto to conduct the extraction (i.e., the weight ratio of extraction solvent: coffee pulp=20:1).

In extraction step, the extraction could be conducted for a suitable period of time depending on the extraction solvent that is adopted. For example, when the extraction solvent is water and the weight ratio of water and the coffee pulp is about 20:1 (water: coffee pulp), the extraction is usually conducted for 0.5 to 3 hours. Furthermore, when conducting the extraction step, other operations such as heating, cooling, stirring, and ultrasonication could be optionally performed to further enhance the extraction efficiency. For example, the extraction could be conducted at 50° C. to 100° C. In one embodiment of the present invention, the extraction was conducted at 85±5° C. for 1 hour. To achieve an extraction efficiency as high as possible, the coffee pulp material could optionally be repeatedly extracted with the same or different extraction solvents, and the liquid extracts thus obtained are combined to provide the liquid extract.

After completing the above extraction step, optional steps such as solid-liquid separation (e.g., filtration, centrifugation), vacuum concentration, drying (e.g., hot-air drying, freeze drying, spray drying), dilution, and sterilization could be carried out to facilitate the use of the liquid extract.

The coffee pulp extract provided in accordance with the present invention could be taken through a transdermal or oral route. For example, the coffee pulp extract could be used as a skin care product such as an emulsion, a cream, a gel (e.g., a hydrogel), or a solution (e.g., an essence, a lotion), or could be used as a form for swallowing or drinking such as a health food product or a beauty beverage, but is not limited thereby. Depending on the form and purpose(s), the skin care product, the health food product, and the beauty beverage those contains the coffee pulp extract provided in accordance with the present invention could be administered at various administration frequencies, such as once a day, multiple times a day, once every few days, etc. In addition, the concentration of the coffee pulp extract in the skin care product, the health food product, and the beauty beverage could be adjusted depending on the requirement of specific population.

The pharmaceutical composition provided in accordance with the present invention could be administered to a subject in need systemically or topically, and could be delivered by various drug delivery systems (DDSs), such as oral drug delivery system, transdermal drug delivery system, injection delivery system, etc. For example, to enhance bioavailability, control drug release speed, target the lesion precisely and reduce side effects, the pharmaceutical composition could be delivered by a liposome, a microcapsule, nanoparticles, microneedles, but is not limited thereby.

Depending on the desired purpose(s), the pharmaceutical composition provided in accordance with the present invention could be provided in any suitable form without particular limitations. For example, the pharmaceutical composition could be administered to a subject in need by an oral or parenteral (such as transdermal administration or subcutaneous injection) route, but is not limited thereby. Depending on the form and purpose(s), a suitable carrier could be chosen and used to provide the pharmaceutical composition. Examples of the carrier include excipients, diluents, auxiliaries, stabilizers, absorption retarders, disintegrating agent, hydrotropic agents, emulsifiers, antioxidants, adhesives, binders, tackifiers, dispersants, suspending agents, lubricants, hygroscopic agents, etc.

As a form for oral administration, the pharmaceutical composition could comprise any pharmaceutically acceptable carrier that will not adversely affect the desired effects of the active ingredient (i.e., coffee pulp extract). Examples of the suitable carrier include, but are not limited to, water, saline, dextrose, glycerol, ethanol or its analogs, oil (e.g., olive oil, castor oil, cottonseed oil, peanut oil, corn oil, germ oil), polyethylene glycol, starch, kaolinite, bentonite, sodium citrate, gelatin, agar, carboxymethyl cellulose, gum arabic, alginic acid and its salts, glyceryl monostearate, calcium stearate, and combinations thereof. The pharmaceutical composition could be provided by any suitable method in any suitable form for oral administration, such as in the form of a tablet (e.g., sugar-coated tablet), a pill, a capsule, granules, a pulvis, a fluidextract, a solution, syrup, a suspension, a tincture, but is not limited thereby.

As a form for transdermal administration, the pharmaceutical composition provided in accordance with the present invention could also comprise any pharmaceutically acceptable carrier that will not adversely affect the desired effects of the active ingredient (i.e., coffee pulp extract). Examples of the suitable carrier include, but are not limited to, water, mineral oil, propylene glycol, polyethylene oxide, liquid petrolatum, sorbitan monostearate, polysorbate 60. The pharmaceutical composition could be provided by any suitable method in any suitable form for transdermal administration, such as in the form of a patch, an emulsion, a cream, a gel (e.g., a hydrogel), a paste (e.g., a dispersing paste, an ointment), a spray, a solution (e.g., a suspension) for external use, but is not limited thereby.

As for the form of injections or drips suitable for subcutaneous administration, the pharmaceutical composition could comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the pharmaceutical composition as an intravenous infusion, an emulsified intravenous infusion, a powder for injection, a suspension for injection, or a powder suspension for injection, etc. Alternatively, the pharmaceutical composition could be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need.

Optionally, the pharmaceutical composition provided in accordance with the present invention could further comprise a suitable amount of additives, such as a flavoring agent, a toner, or a coloring agent for enhancing the palatability and the visual perception of the pharmaceutical composition, and/or a buffer, a conservative, a preservative, an antibacterial agent, or an antifungal agent for improving the stability and storability of the pharmaceutical composition. In addition, the pharmaceutical composition could optionally further comprise one or more other active ingredient(s) to further enhance the effect of the pharmaceutical composition, or to increase the application flexibility and adaptability of the preparation thus provided, as long as the other active ingredients do not adversely affect the desired effects of the active ingredient of the present invention (i.e., coffee pulp extract).

Depending on the needs, age, body weight and health conditions of the subject, the pharmaceutical composition provided in accordance with the present invention could be administered at various administration frequencies, such as once a day, multiple times a day, once every few days, etc. In addition, the concentration of the coffee pulp extract in the pharmaceutical composition could be adjusted depending on the requirements of practical application.

The present invention also provides a method for at least one of whitening skin, improving skin condition, protecting skin, and/or inhibiting skin aging, comprising administering to a subject in need an effective amount of a coffee pulp extract, wherein the term "a subject in need" refers to a subject having a requirement for improving skin condition and/or preventing the skin condition from getting worse. For example, the subject is one having thickening of skin keratin, generation of skin wrinkles, generation of skin spots, skin dullness, desiccation and desquamation of skin, skin sagging, and/or skin aging, or one working outdoors for a long time, but is not limited thereby. In the method, the coffee pulp extract could be administered to the subject as a skin care product, a health food product, or a beauty beverage. The administration form, administration frequency and uses of the skin care product, the health food product, and the beauty beverage are all in line with the above descriptions.

The present invention also provides a method for at least one of repairing skin tissues, preventing skin disease, and treating skin disease, comprising administering to a subject in need an effective amount of a coffee pulp extract, wherein the term "a subject in need" refers to a subject having skin lesion phenomena, suffering from skin disease, and/or with high risk of skin disease. For example, the subject is one suffering from a disease related to dry skin, and/or with high risk of a disease related to dry skin. In the method, the coffee pulp extract could be administered to the subject as a pharmaceutical composition. The administration type, administration route, administration form, administration frequency and uses of the pharmaceutical composition are also all in line with the above descriptions.

The present invention also provides a method for increasing the expressions of KRT1 gene, KRT14 gene, AQP3 gene, FLG gene, GBA gene, HAS2 gene and/or HAS3 gene, comprising administering to a subject in need an effective amount of a coffee pulp extract, wherein the term "a subject in need" refers to a subject whose KRT1 gene, KRT14 gene, AQP3 gene, FLG gene, GBA gene, HAS2 gene and/or HAS3 gene is deleted, mutated, or low-expressed. In the method, the coffee pulp extract could be administered to the subject in need as a pharmaceutical composition. The administration type, administration route, administration form, administration frequency and uses of the pharmaceutical composition are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Preparation Examples

A. Preparation of Coffee Pulp Extract

The coffee fruits (*Arabica* species; provided by Grand ALISHAN Premium Coffee Cooperative, Taiwan) were shelled, and then, the coffee pulps were taken out and collected. Then, the coffee pulps were subjected to the following steps to provide a coffee pulp extract:

1. Placing 100 g of coffee pulps and 2000 mL of water into a container and mix evenly, and then subjecting the mixture thus obtained to an extraction at 85±5° C. for 1 hour to provide a liquid extract;
2. Cooling the liquid extract to the room temperature, and then filtrating the same with a 400-mesh filter to provide a filtrate; and
3. Concentrating the filtrate under vacuum at 45° C. to 70° C. to provide a concentrated liquid extract (i.e., coffee pulp extract of the present invention; hereinafter referred to as "primary coffee pulp extract liquid").
4. Sterilizing the concentrated liquid extract by ultra-high temperature processing (UHT), and then subject the same to a spray drying to provide a powder (hereinafter referred to as "coffee pulp extract powder").

B. Dilution of Coffee Pulp Extract

The primary coffee pulp extract liquid provided by [Preparation Example A] was subjected to a 2-fold dilution, a 10-fold dilution and a 100-fold dilution, to provide three diluted coffee pulp extract liquids having concentrations of 50%, 10% and 1%, respectively.

C. Preparation of Collagen Solution and Fructose Solution

A 60 mg/ml collagen solution (containing 0.06% sodium azide) and a 1.5M D-fructose solution were prepared respectively by using 200 mM phosphate buffer (pH=7.4) as the solvent.

D. Preparation of Aminoguanidine (AG) Solution

A 3 mM aminoguanidine (AG) solution was prepared by using 200 mM phosphate buffer (pH=7.4) as the solvent.

E. Preparation of Glycosylated Bovine Serum Albumin (BSA)

The glucose purchased from Sigma company was formulated into a 0.5M glucose solution by using PBS as the solvent. Then, the bovine serum albumin (BSA) purchased from Bio Basic Inc. (product number: AD0023) was formulated into a 50 mg/mL BSA solution by using the 0.5M glucose solution as the solvent. Thereafter, the 50 mg/mL BSA solution was kept in an oven of 70° C. for four days to induce the glycosylation of BSA, thereby providing a glycosylated BSA.

Example 1

Effect of Coffee Pulp Extract on Inhibiting Glycosylation (Anti-Glycosylation)

To determine whether the coffee pulp extract of the present invention can inhibit glycosylation of protein in skin cells, the production level of advanced glycation end products (AGEs) was examined by the following experiments.

A. Experimental groups:
  I. Preparing five mixed solutions by evenly mixing 0.2 mL of collagen solution and 0.2 mL of fructose solution provided by [Preparation Example C] with 0.2 mL each of the primary coffee pulp extract liquid provided by [Preparation Example A], the diluted coffee pulp extract liquid having a concentration of 50% provided by [Preparation Example B], the diluted coffee pulp extract liquid having a concentration of 10% provided by [Preparation Example B], and the diluted coffee pulp extract liquid having a concentration of 1% provided by [Preparation Example B], respectively;
  II. Keeping the mixed solutions provided by step I at 50° C. for 24 hours to induce glycosylation of the collagen in the solutions, and thus obtain five glycosylation solutions; and
  III. Respectively measuring the fluorescence values of mixed solutions provided by step I and glycosylation solutions provided by step II (0.1 mL each of mixed solution and glycosylation solution was used) at an excitation light wavelength of 360 nm and an emission light wavelength of 460 nm (i.e., the fluorescence value of mixed solution is called as "0-hr fluorescence value of experimental group, and the fluorescence value of glycosylation solution is called as "24-hr fluorescence value of experimental group).

B. Control group:
  i. Preparing a mixed solution by mixing 0.2 mL of water with 0.2 mL of collagen solution and 0.2 mL of fructose solution provided by [Preparation Example C] evenly;
  ii. Keeping the mixed solution provided by step i at 50° C. for 24 hours to induce glycosylation of the collagen in the solution, and thus obtain a glycosylation solution; and
  iii. Respectively measuring the fluorescence values of mixed solution provided by step i and glycosylation solution provided by step ii (0.1 mL each of mixed solution and glycosylation solution was used) at an excitation light wavelength of 360 nm and an emission light wavelength of 460 nm (i.e., the fluorescence value of mixed solution is called as "0-hr fluorescence value of control group, and the fluorescence value of glycosylation solution is called as "24-hr fluorescence value of control group).

C. Positive control group: the experimentation steps were the same as those of experimental groups, but the primary coffee pulp extract liquid and the diluted coffee pulp extract liquids used for the experimental groups were replaced by the AG solution provided by [preparation Example D].

Thereafter, the production level of AGEs (%) of each experimental group was calculated by the following formula, and the results are shown in FIG. 1.

Production level of $AGEs$ $$(\%) = \left[ \frac{\text{24-hr fluorescence of experimental group} - \text{0-hr fluorescence of experimental group}}{\text{24-hr fluorescence of control group} - \text{0-hr fluorescence of control group}} \right] \times 100\%$$

As shown in FIG. 1, the primary coffee pulp extract liquid, the diluted coffee pulp extract liquid having a concentration of 50%, and the diluted coffee pulp extract liquid having a concentration of 10% all are effective in inhibiting the production of AGEs. These results indicate that the coffee pulp extract of the present invention can indeed effectively inhibit glycosylation of protein (anti-glycosylation).

Example 2

Effect of Coffee Pulp Extract on Inhibiting Oxidative Stress

The following experimentation was conducted to determine whether the coffee pulp extract of the present invention can inhibit oxidative stress. First, human skin fibroblasts (CCD-966sk; purchased from BCRC, product number: 60153) were cultured in a MEM medium (minimum essential medium; purchased from Gibco company, product number: 61100-061) for 24 hours. Thereafter, the cells were divided into three groups and independently subjected to the following treatments:

(1) Control group: cells were continuously cultured in a MEM medium for 24 hours.
(2) AGEs group: cells were continuously cultured in a MEM medium for 24 hours, and then 0.4 mL of glycosylated BSA provided by [Preparation Example E] was added into the medium to continuously culture the cells for 3 hours.
(3) Extract group: cells were continuously cultured in a MEM medium that contains 0.25 mg of the primary coffee pulp extract liquid provided by [Preparation Example A] per mL for 24 hours, and then 0.4 mL of glycosylated BSA provided by [Preparation Example E] was added into the medium to continuously culture the cells for 3 hours.

Thereafter, the cells in each group were treated with DCFH-DA dye (purchased from Sigma company, product number: SI-D6883-50MG) for 15 minutes, and then, washed with PBS twice and suspended in PBS, to provide a cell solution. The cell solution was added with 200 µL of Trypsin to react in a dark environment for 5 minutes, and then, placed in a 15 mL centrifuge tube and subjected to a centrifugation at 400 g for 10 minutes. The supernatant was removed, and then the cells were washed with PBS once and subjected to a centrifugation at 400 g for 10 minutes again. Finally, the cell precipitate thus obtained was resuspended with PBS, and then the fluorescence values of the cells in each group were detected by a flow cytometry at the excitation wavelength of 450 nm to 490 nm and the emission wavelength of 510 nm to 550 nm. Because ROS can convert DCFH-DA (without fluorescence) into DCF (with fluorescence), the fluorescence value can represent the content of ROS in cells, and the higher fluorescence value represents the higher content of ROS in cells. The data was analyzed by Student t-test in Excel, and the result of "Control group" was used as a basis to calculate the content of ROS in cells of each other group. The results are shown in FIG. 2.

Figure 2:
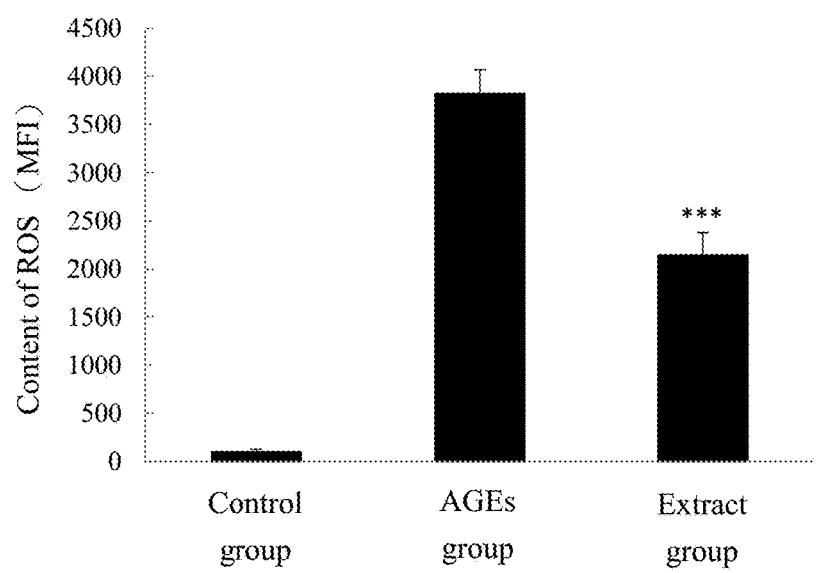
FIG. 2 shows the effect of the coffee pulp extract of the present invention on inhibiting oxidative stress, wherein the cells in "Control group" were cultured in a medium free of coffee pulp extract for 24 hours, those in the "AGEs group" were cultured in a medium free of coffee pulp extract for 24 hours and then treated with glycosylated BSA for 3 hours, and those in the "Extract group" were cultured in a medium that contains the coffee pulp extract for 24 hours and then treated with glycosylated BSA for 3 hours (*** represents the result is significantly different from that of "AGEs group", $p<0.001$)

As shown in FIG. 2, as compared to "Control group", the content of ROS in "AGEs group" significantly increased. However, as compared to "AGEs group", the contents of ROS in "Extract group" significantly decreased. These results indicate that glycosylation can lead to increase of oxidative stress in cells, and coffee pulp extract of the present invention can effectively inhibit the oxidative stress caused by glycosylation and thus is effective in anti-oxidation.

Example 3

Effect of Coffee Pulp Extract on Increasing Skin Tightness

To determine whether the coffee pulp extract of the present invention is effective in increasing skin tightness, human skin fibroblasts (CCD-966sk; purchased from BCRC, product number: 60153) were cultured in a MEM medium for 24 hours. Thereafter, the cells were divided into three groups and independently subjected to the following treatments:

A. Control group:
1. Using 500 μL as a basis of volume, depositing 0.66 volume of cells in a sterile tube, and adding thereinto 0.33 volume of 3 mg/mL Type I collagen (purchased from Gibco company, product number: A10483-01) solution, then quickly adding thereinto an appropriate amount of 1M sodium hydroxide solution (the amount of sodium hydroxide solution should be that can at least convert phenol red medium indicator into light pink color), and then, mixing the solution up and down three times, to provide a mixture;
2. Depositing 500 μL of the mixture provided by step 1 in a 24-well culture plate, and keeping the plate at room temperature for 20 minutes to solidify the mixture into a gel; and
3. Adding 500 μL of MEM medium into the plate, and carefully separating the surrounding of the gel from the plate to suspend the gel in the MEM medium, and then depositing the plate in an incubator of 37° C. and 5% $CO_2$ for 6 hours.

B. AGEs group:
(1) Using 500 μL as a basis of volume, depositing 0.66 volume of cells in a sterile tube, and adding thereinto 0.33 volume of 3 mg/mL Type I collagen (purchased from Gibco company, product number: A10483-01) solution, and quickly adding thereinto an appropriate amount of 1M sodium hydroxide solution (the amount of sodium hydroxide solution should be that at least can convert phenol red medium indicator into light pink color), adding glycosylated B SA provided by [Preparation Example E], and then mixing the solution up and down three times, to provide a mixture;
(2) Depositing 500 μL of the mixture provided by step (1) in a 24-well culture plate, and keeping the plate at room temperature for 20 minutes to solidify the mixture into a gel; and
(3) Adding 500 μL of MEM medium into the plate, and carefully separating the surrounding of the gel from the plate to suspend the gel in the MEM medium, and then depositing the plate in an incubator of 37° C. and 5% $CO_2$ for 6 hours.

C. Extract group: the preparation steps were the same as those of "AGEs group", but in step (3), before the plate was deposited in the incubator, the primary coffee pulp extract liquid provided by [Preparation Example A] was further added into the MEM medium to the final concentration of 0.25 mg/mL.

Then, in a period of 6 hours, the appearances of the gels were observed and recorded by a digital camera every 3 hours. The photographs took at the $6^{th}$ hour was analyzed by Image J software to calculate the surface area of the gel of each group (the smaller surface area of the gel represents stronger contraction ability). Finally, the data thus obtained was analyzed by Student t-test, and the result of "Control group" was used as a basis (i.e., the contraction ability of "Control group" was set as 100%) to calculate the contraction abilities of the gels of "AGEs group" and "Extract group". The results are shown in FIGS. 3A and 3B.

Figure 3A:
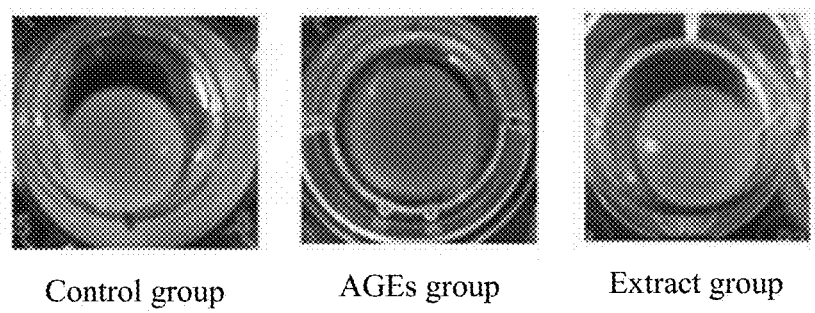
Figure 3B:
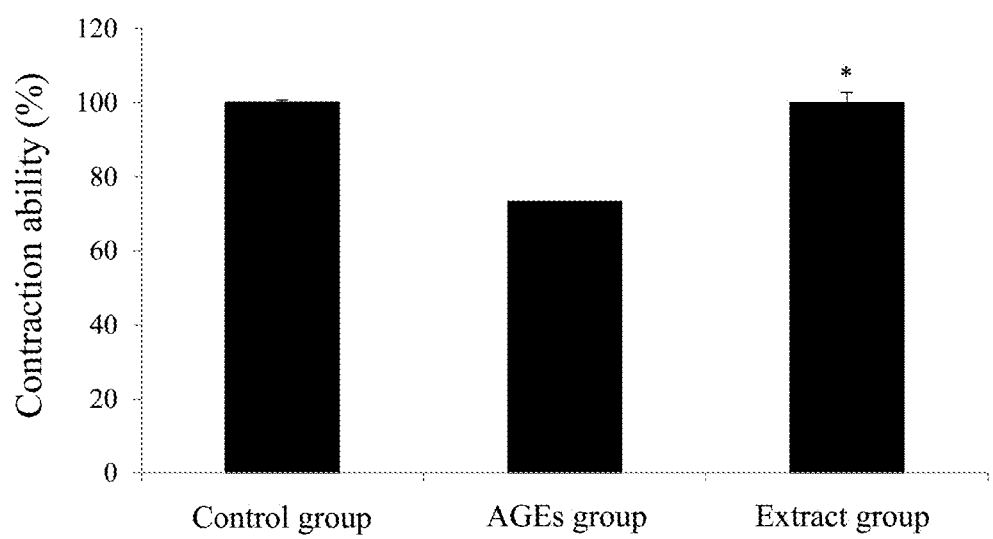
Figure 4:
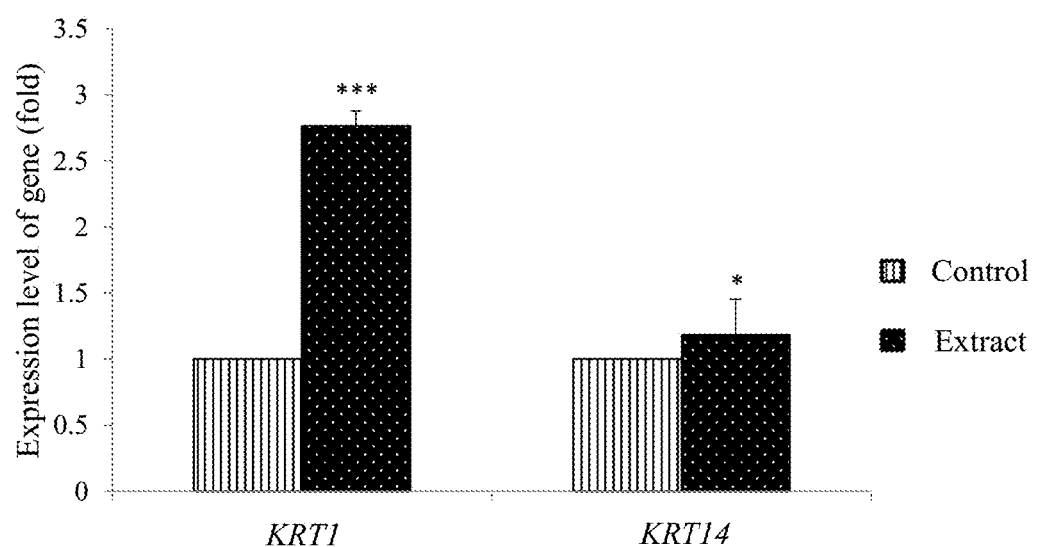
Figure 5:
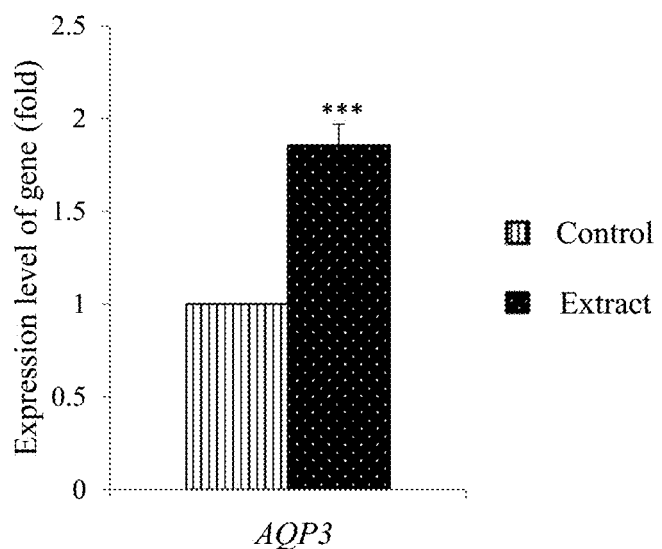
Figure 6:
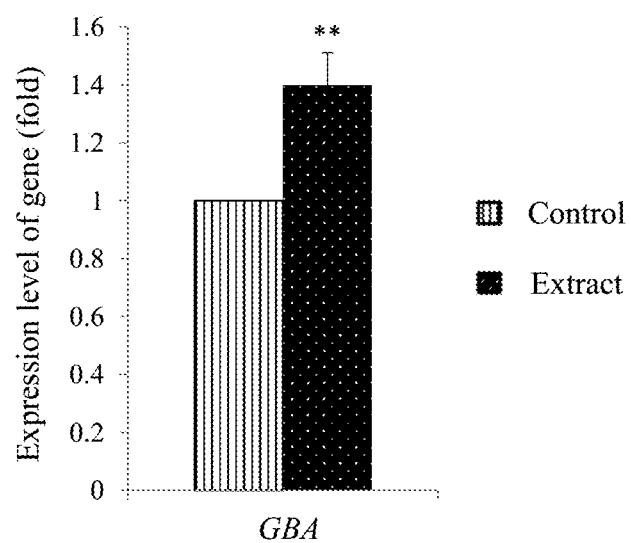
Figure 7:
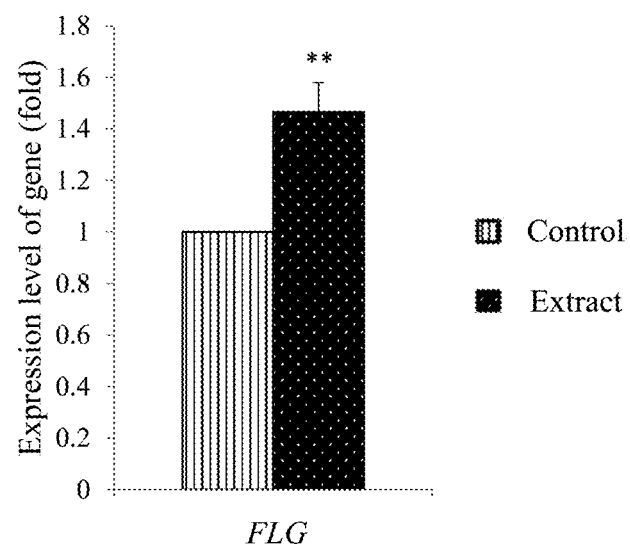
Figure 8:
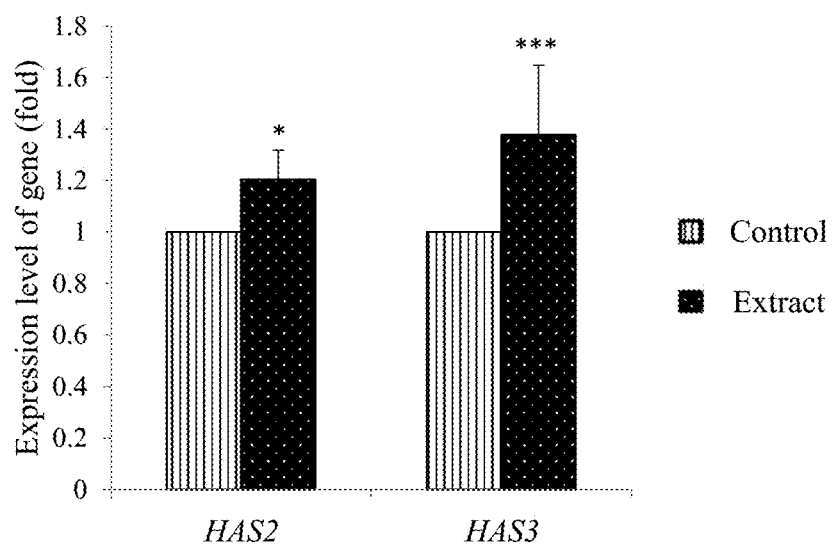
Figure 9:
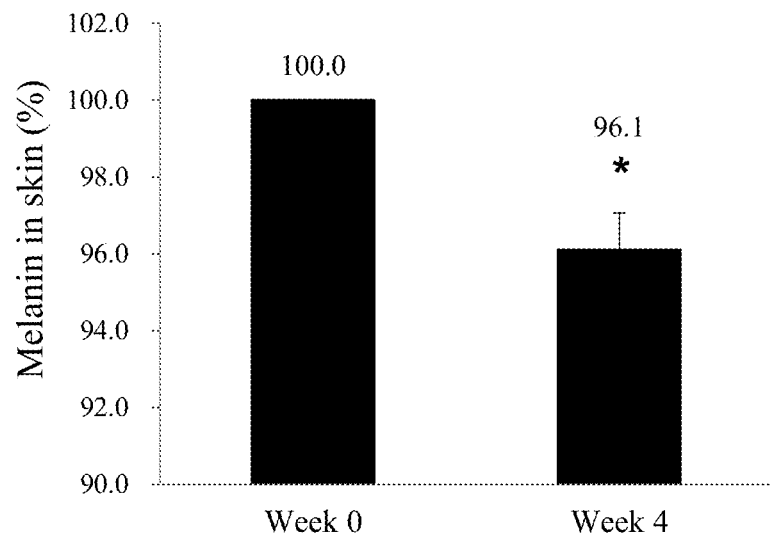
FIG. 9, FIG. 10, FIG. 11, FIG. 12 and FIG. 13 respectively show the effects of the coffee pulp extract of the present invention on reducing melanin in skin, reducing brown spots on skin, increasing water content of skin, increasing skin elasticity and enhancing skin brightness (* represents the result is significantly different from that of "Week 0", $p<0.05$)
Figure 10:
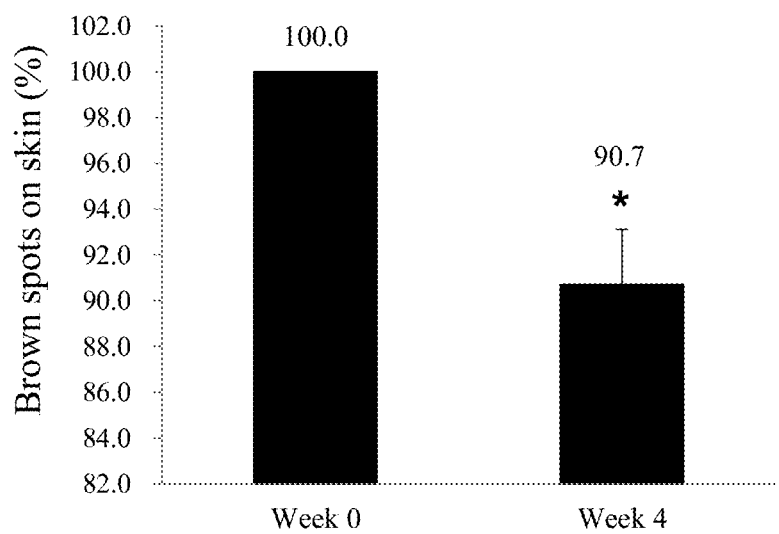
Figure 11:
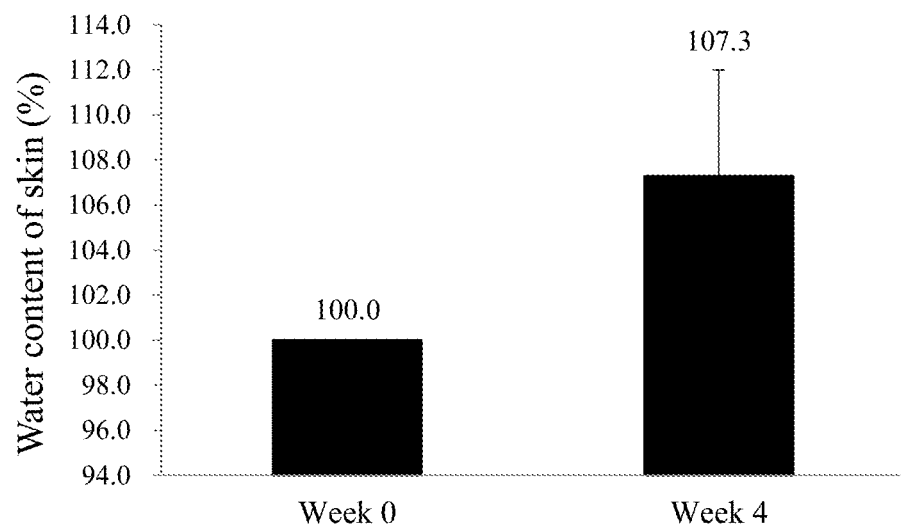
Figure 12:
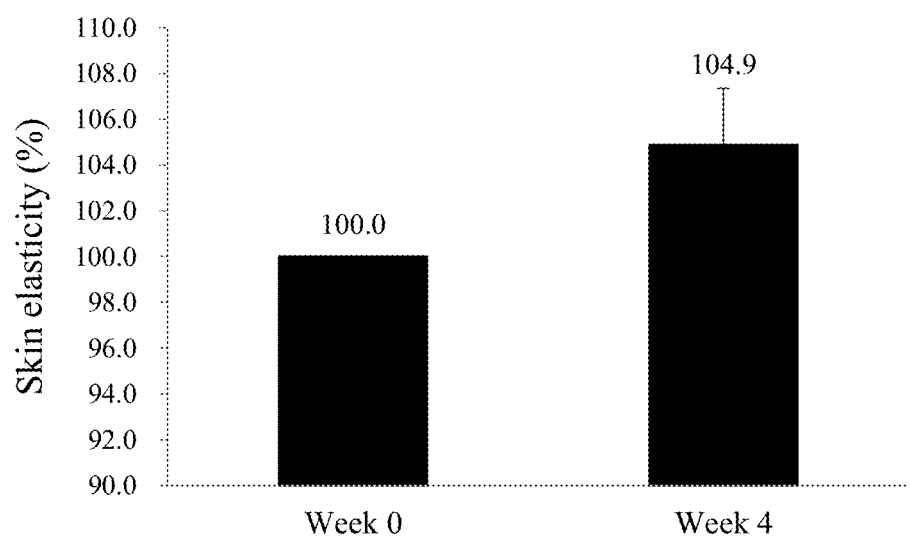
Figure 13:
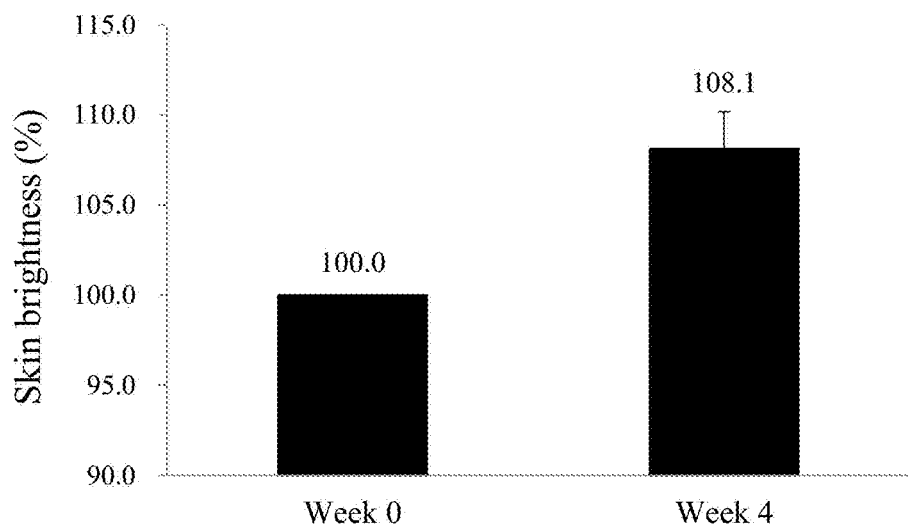

As shown in FIGS. 3A and 3B, as compared to "Control group", the appearance and surface area of the gel of "AGEs group" are significantly larger, which indicates that the stimulation of glycosylated BSA may cause hardening and break of collagen in the gel and thus result in sagging. However, as compared to "AGEs group", the appearance and surface area of the gel of "AGEs group" are significantly smaller, and even same as that of "Control group". These results indicate that coffee pulp extract of the present invention is indeed effective in increasing skin tightness, and thus, can be used for tightening skin and reducing skin fine lines.

Example 4

Effect of Coffee Pulp Extract on Increasing the Expressions of KRT1 Gene, KRT14 Gene, AQP3 Gene, FLG Gene, GBA Gene, HAS2 Gene HAS3 Gene As described above, if the expressions of KRT1 gene, KRT14 gene, AQP3 gene, FLG gene, GBA gene, HAS2 gene and HAS3 gene in skin cells can be increased, the following effects could be provided: assisting in maintenance of skin health, moisturizing skin, tightening skin, reducing skin fine lines, inhibiting skin aging, alleviating dry skin, preventing skin disease, and/or treating skin disease. To determine whether the coffee pulp extract is effective in increasing the expressions of KRT1 gene, KRT14 gene, AQP3 gene, FLG gene, GBA gene, HAS2 gene HAS3 gene in skin cells, human primary epidermal keratinocytes (HPEK-50; purchased from CELLnTEC, product number: CNT-PR-3D) were cultured in a SFM medium (serum free medium; purchased from Gibco company, product number: 17005042) for 24 hours. Then, the cells were divided into two groups and independently subjected to the following treatments:
(1) Control group: cells were cultured in a SFM medium for 6 hours.
(2) Extract group: cells were cultured in a SFM medium that contains 0.25 mg of the primary coffee pulp extract liquid provided by [Preparation Example A] per mL for 6 hours.

Thereafter, cells in each group were harvested and subjected to an RNA extraction with an RNA extraction kit (purchased from Geneaid company). Then, the RNA thus provided was transcribed into cDNA by using a reverse transcriptase (SuperScript® III Reverse Transcriptase; purchased from Invitrogen company). The cDNA thus provided was subjected to a quantitative polymerase chain reaction (qPCR) by using an ABI Step One Plus system and a KAPA SYBR FAST qPCR kit to determine the expression levels of KRT1 gene, KRT14 gene, AQP3 gene, FLG gene, GBA gene, HAS2 gene and HAS3 gene. Finally, the data thus obtained was analyzed by T.TEST of Excel (one tailed Student's t-test), and the result of "Control group" was used as a basis (i.e., the gene expression level of "Control group" was set as 1-fold) to calculate the relative gene expression levels of the other groups. The results are shown in FIGS. 4 to 8.

As shown in FIGS. 4 to 8, as compared to "Control group", the expression levels of KRT1 gene, KRT14 gene, AQP3 gene, FLG gene, GBA gene, HAS2 gene and HAS3 gene all significantly increased. These results indicate that coffee pulp extract of the present invention can indeed effectively increase the expression levels of KRT1 gene, KRT14 gene, AQP3 gene, FLG gene, GBA gene, HAS2 gene and HAS3 gene, and thus, can be used for assisting in maintenance of cell structure, assisting in the formation of skin barrier, enhancing hyaluronic acid synthesis, and increasing the water content of cells, thereby providing the effects of assisting in maintenance of skin health, moisturizing skin, tightening skin, reducing skin fine lines, inhibiting skin aging, and alleviating dry skin, and can be used for preventing a disease related to dry skin, and/or a disease related to dry skin.

Example 5

Human Clinical Trials (5-1) Long-Term Trial of Eating Coffee Pulp Extract

This experimentation was carried out in a self-control way by eight people (eight subjects) between 30 to 55 years old. Each subject drunk a bottle of coffee pulp beverage (containing 0.14% primary coffee pulp extract liquid provided by [Preparation Example A], based on the total weight of the beverage) for 4 weeks. The brown spots on skin were detected and recorded by using a VISIA Complexion Analysis System (purchased from Canfield company, U.S.) at week 0 (i.e., prior to starting drinking the coffee pulp beverage containing the coffee pulp extract of the present invention) and week 4 (i.e., after drinking the coffee pulp beverage containing the coffee pulp extract of the present invention for 4 weeks), respectively. And, the melanin in skin, water content of skin, skin elasticity and skin brightness were detected and recorded by using a C+K Cutometer® dual MPA580 multiprobes skin analyzer (purchased from C+K electronic company, Germany) at week 0 and week 4. In addition, the facial skin of each subject was captured by using a high-resolution single lens reflex camera with three light sources (including full-wavelength, ultraviolet, and polarized-wavelength) to observe skin condition. Then, the data thus obtained was analyzed by Student t-test, and the result of week 0 was used as a basis (i.e., the result of week 0 was set as 100%) to calculate the melanin in skin, brown spots on skin and water content of skin, skin elasticity and skin brightness after drinking the coffee pulp beverage containing the coffee pulp extract of the present invention for 4 weeks. The results are shown in FIGS. 9 to 13.

As shown in FIGS. 9 to 13, after drinking the coffee pulp beverage containing the coffee pulp extract of the present invention for 4 weeks, the melanin in skin and brown spots on skin of the subjects significantly reduced, and the water content of skin, skin elasticity and skin brightness of the subjects significantly increased. These results indicate that coffee pulp extract of the present invention is indeed effective in reducing melanin in skin, reducing spots on skin, moisturizing skin, increasing skin elasticity and enhancing skin brightness.

(5-2) Short-Term Trial of Applying Coffee Pulp Mask

The experimentation was carried out in a self-control way by five people (five subjects). Each subject applied the coffee pulp mask (containing 2% primary coffee pulp extract liquid provided by [Preparation Example A], based on the total weight of the essence in mask) over half side of their face and applied the placebo mask (free of the primary coffee pulp extract liquid of the present invention, but other ingredients all were same as the coffee pulp mask) to the other half side of their face, and the skin was massaged gently with finger pulps for 15 minutes to enhance the absorption of the essence in the mask. The skin elasticity was detected and recorded by using a C+K Cutometer® dual MPA580 multiprobes skin analyzer (purchased from C+K electronic company, Germany) at 0 minute (i.e., prior to starting applying the mask) and $15^{th}$ minute (i.e., after applying the mask drinking for 15 minutes), respectively. Then, the data thus obtained was analyzed by Student t-test, and the result of 0 minute was used as a basis (i.e., the result of 0 minute was set as 100%) to calculate the skin elasticity after applying the mask for 15 minutes. The results are shown in FIG. 14.

Figure 14:
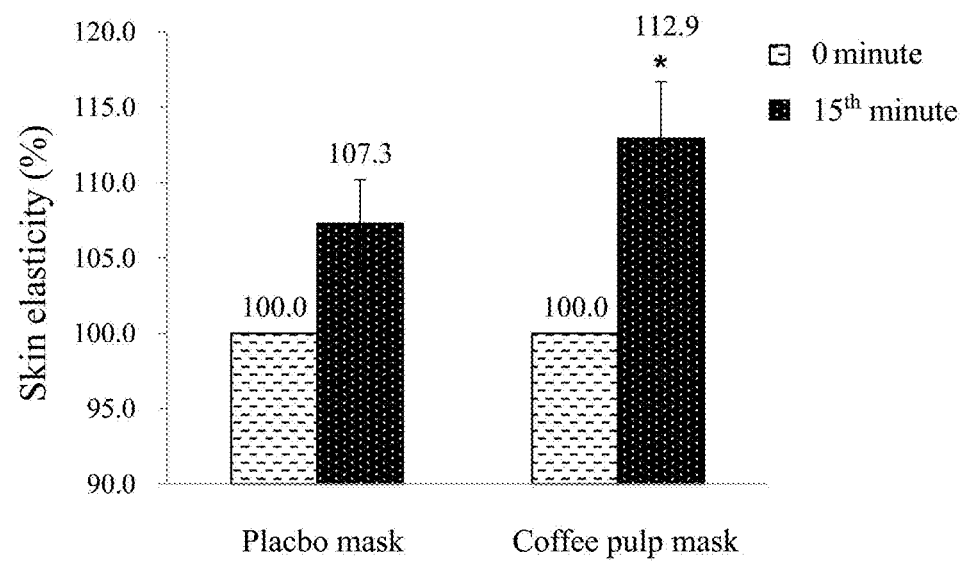
FIG. 14 shows the effect of coffee pulp extract of the present invention on increasing skin elasticity (* represents the result is significantly different from that of "0 minute", $p<0.05$).

As shown in FIG. 14, as compared to the placebo mask, after applying the coffee pulp mask for 15 minutes, the skin elasticity of the subjects significantly increased. This result indicates that coffee pulp extract of the present invention is effective in increasing skin elasticity in a short period of time.

What is claimed is:

1. A method of repairing skin tissues, comprising administering to a subject in need thereof, an effective amount of a composition comprising a coffee pulp extract and a carrier, wherein the composition is administered to the subject by oral administration.

2. The method as claimed in claim 1, wherein the extract is provided by extracting coffee pulp with a polar solvent, wherein the polar solvent is selected from the group consisting of water, C1-C4 alcohols, and combinations thereof.

3. The method as claimed in claim 1, which is for inhibiting protein glycosylation in skin cells, and/or decreasing oxidative stress-induced damage to skin cells.

4. The method as claimed in claim 1, which is for treating diseases related to dry skin.

* * * * *